US00PP36245P2

(12) United States Plant Patent
Scheys

(10) Patent No.: US PP36,245 P2
(45) Date of Patent: Nov. 5, 2024

(54) ***HEUCHERA* PLANT NAMED 'Snowy Panky'**

(50) Latin Name: ***Heuchera* hybrid**
Varietal Denomination: Snowy Panky

(71) Applicant: Diederik Alexander Maria Scheys, Torcé-Viviers en Charnie (FR)

(72) Inventor: Diederik Alexander Maria Scheys, Torcé-Viviers en Charnie (FR)

( * ) Notice: Subject to any disclaimer, the term of this patent is extended or adjusted under 35 U.S.C. 154(b) by 0 days.

(21) Appl. No.: 18/507,453

(22) Filed: Nov. 13, 2023

Related U.S. Application Data

(60) Provisional application No. 63/432,766, filed on Dec. 15, 2022.

(51) Int. Cl.
*A01H 5/12* (2018.01)
*A01H 6/80* (2018.01)

(52) U.S. Cl.
USPC ..... Plt./440

(58) Field of Classification Search
USPC ..... Plt./440
See application file for complete search history.

*Primary Examiner* — Susan McCormick Ewoldt
(74) *Attorney, Agent, or Firm* — Penny J. Aguirre

(57) ABSTRACT

A new cultivar of *Heuchera* plant named 'Snowy Panky' that is characterized by its glossy foliage that is green in color and are mottled white with red to purple veins and flowers that are fuchsia pink in color.

2 Drawing Sheets

Botanical classification: *Heuchera* hybrid.
Cultivar designation: 'Snowy Panky'.

BACKGROUND OF THE INVENTION

The present invention relates to a new and distinct cultivar of *Heuchera* of hybrid origin, botanically known as *Heuchera* 'Snowy Panky' and is hereinafter referred to by its cultivar name 'Snowy Panky'.

'Snowy Panky' originated as a seedling that arose from seed planted from open pollination of an unnamed and unpatented plant of *Heuchera* from the Inventors' breeding program a trial garden in Réty, France. The male parent is therefore unknown. 'Snowy Panky' was selected as a single unique plant in June 2017 from the resulting seedlings.

Asexual propagation of the new cultivar was first accomplished under the direction of the Inventor by tissue culture initiated from meristem tissue in September of 2019 in Beervelde, Belgium. Asexual propagation of the new cultivar by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Snowy Panky' as a new and unique cultivar of *Heuchera*.

1. 'Snowy Panky' exhibits glossy foliage that is green in color and are mottled white with red to purple veins.
2. 'Snowy Panky' exhibits flowers that are fuchsia pink in color.

The female parent plant of 'Snowy Panky' differs from 'Snowy Panky' in having leaves that are less mottled with white, leaf veins that are not red to purple in color, and flowers that are light pink in color. 'Snowy Panky' can be most closely compared to the *Heuchera* cultivars 'Snow Angel' (not patented) and 'Snow Storm' (not patented). Both 'Snow Angel' and 'Snow Storm' are similar to 'Snowy Panky' in having variegated foliage. 'Snow Angel' differs from 'Snowy Panky' in having foliage with large blotches of white with rare pink coloration but lacks red to purple veins. 'Snow Storm' differs from 'Snowy Panky' in having foliage that is more white in color (more heavily mottled) with rare pink coloration but lacks red to purple veins.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Denis Plants, Pepiniere des Deux Caps, Promesse de Fleurs, Happy Youchera, Floriculture International (Plantarium), Vaste Planten Perennials, Luckbridge Horticulture, Hortweek, Hogendoorn, Plant Estate, and Podsadzone.

BRIEF DESCRIPTION OF THE DRAWINGS

The accompanying color photographs illustrate the overall appearance and distinct characteristics of the new *Heuchera*. The photographs in FIG. 1 and FIG. 3 were taken of a plant 16 months in age as grown outdoors in a 12-cm container in Torcé Viviers en Charnie, France. The photograph in FIG. 2 was taken of plants about 4 months in age as grown outdoors as in a 12-cm container (several in one container) in Beervelde, Belgium.

The photograph in FIG. 1 provides a side view of 'Snowy Panky' in bloom.

Figure 1:
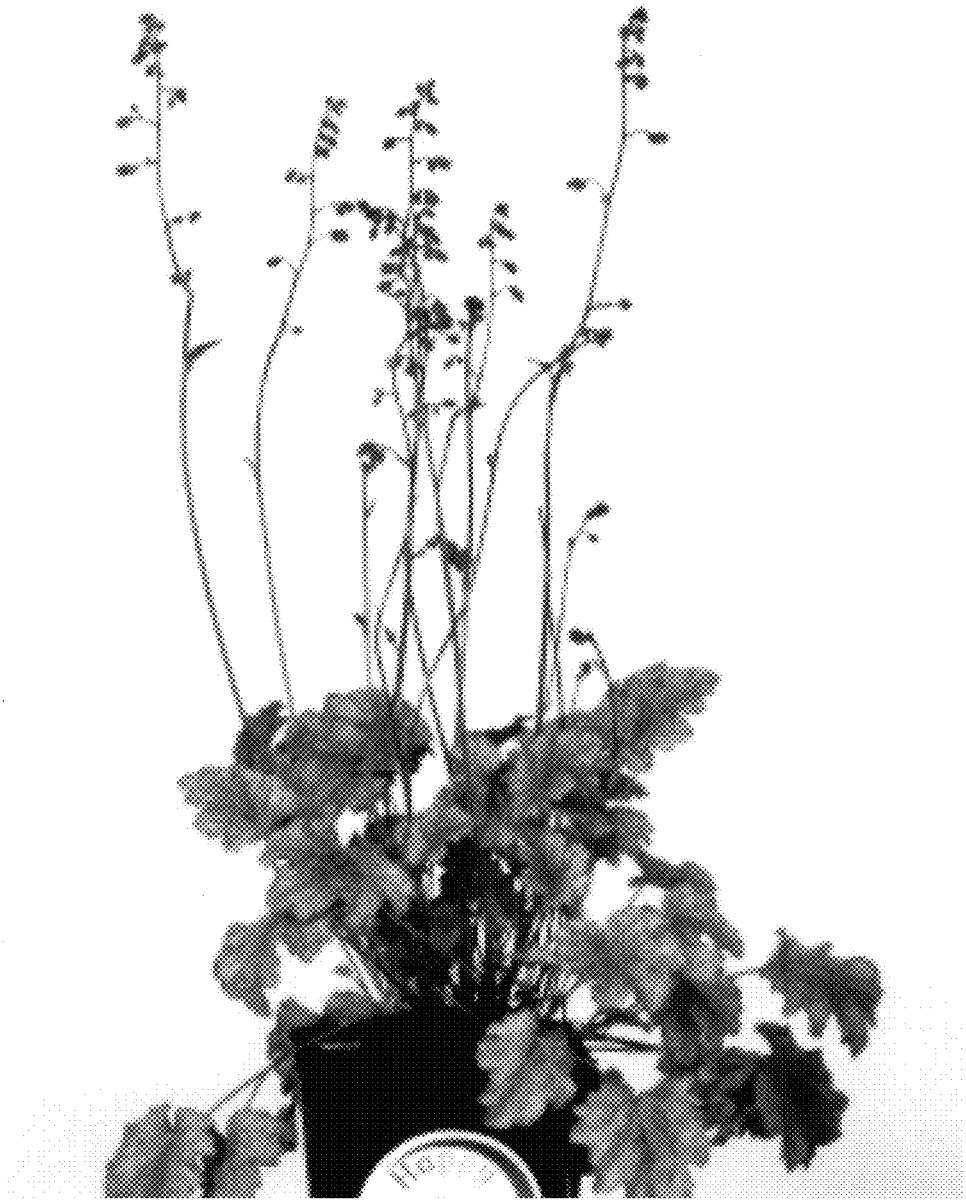
Figure 2:
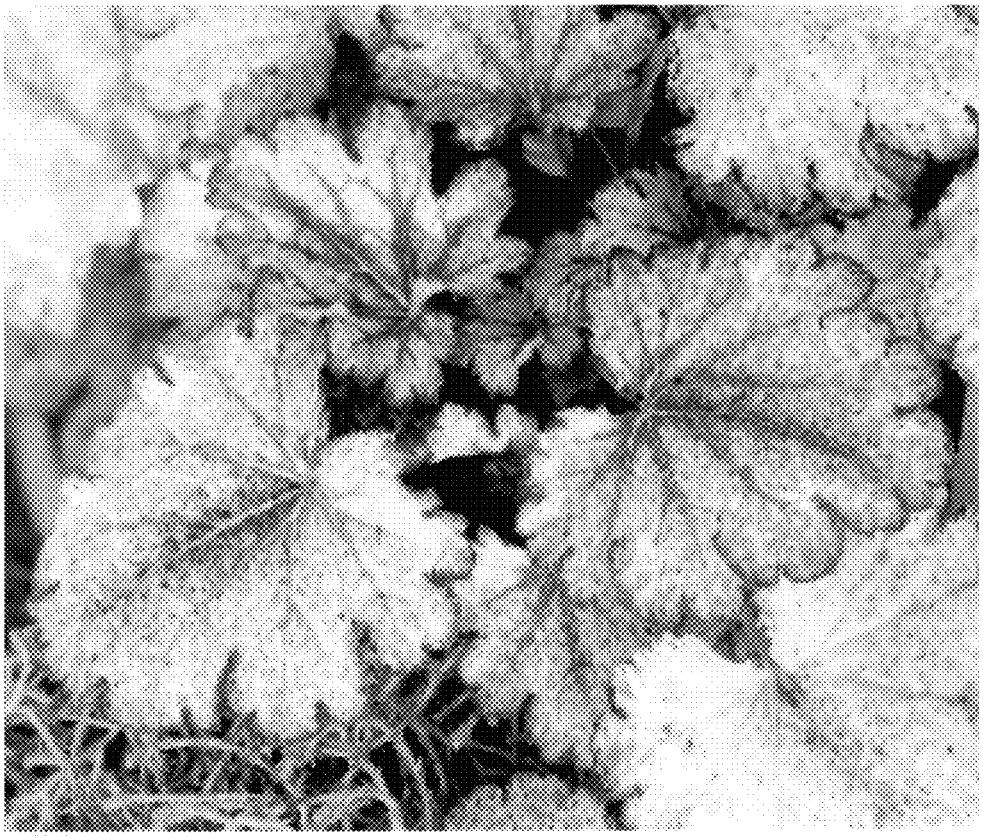

The photograph in FIG. 2 provides a close up view of the young foliage of 'Snowy Panky'.

Figure 3:
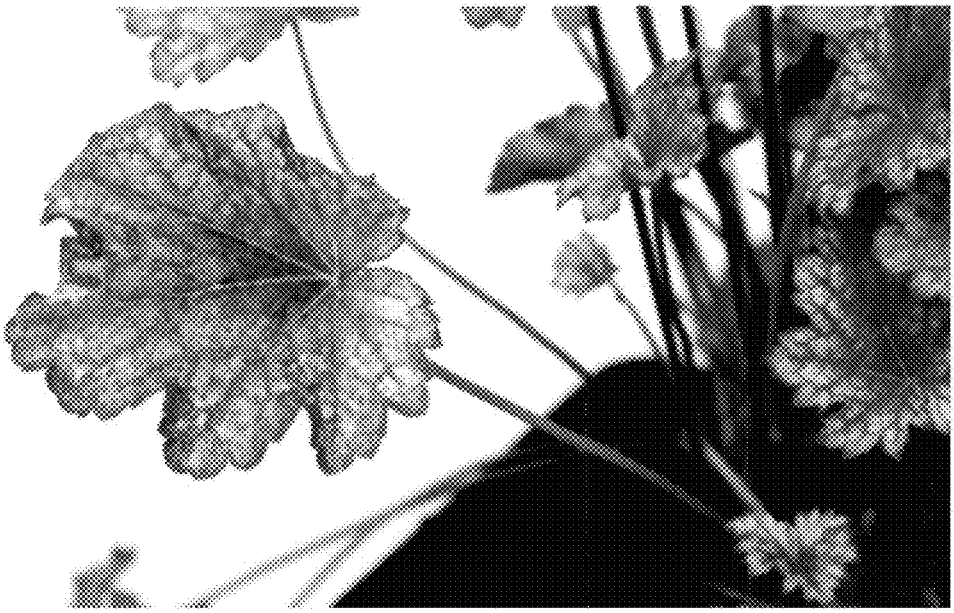

The photograph in FIG. 3 provides a close up view of the mature foliage of 'Snowy Panky'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 16-month-old plants of 'Snowy Panky' as grown outdoors in 12-cm square containers in Torcé Viviers en Charnie, France. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming period*.—April to June in The Netherlands.

*Plant type*.—Herbaceous perennial.

*Plant habit*.—Globular with inflorescences held above the foliage.

*Height and spread*.—An average of 20 cm in height (soil level to top of foliar plane), 53 cm (soil level to top of floral plane), and 37 cm in spread as a 16-month-old plant in a container.

*Hardiness*.—At least in U.S.D.A. Zones 4 to 9.

*Diseases and pests*.—No susceptibility or resistance to pests or diseases has been observed.

*Root description*.—Fibrous roots on woody rootstalks.

*Propagation*.—Tissue culture.

*Root development*.—An average of 3 weeks for root initiation and 6 weeks to produce a rooted cutting.

*Growth rate*.—Moderate.

*Branching habit*.—Flowering stems emerge from basal rosette.

Foliage description:

*Leaf shape*.—Broad ovate to nearly reniform in outline.

*Leaf division*.—Simple.

*Leaf base*.—Hastate, lobes free to touching.

*Leaf apex*.—Obtuse to very short and abruptly acute.

*Leaf venation*.—Reticulate, color; upper surface 150D, lower surface 145B, occasionally tinged with 51D.

*Leaf margins*.—Crenate, each lobe with an obtuse to very short abruptly acute tip, margin moderately undulate, moderately covered with very short hairs.

*Leaf attachment*.—Petiolate.

*Leaf arrangement*.—Alternate in basal rosettes.

*Leaf lobes*.—Lobed, an average of 9 lobes, shallow in depth, divergent, lobe margins free.

*Leaf surface*.—Both surfaces are smooth, non-rugose, and pubescent, densely covered with short strigose hairs; 0.2 mm in length, translucent, upper surface is very slightly glossy, lower surface is matte.

*Leaf color*.—Young upper surface; 145C and 145D with the areas surrounding the venation a blend of 53B to 53D, 59C and 60A, — edges of margins 137C and 143A, young lower surface; a blend of 51B, 51C and 185D, margins and top 145C, edges of margins 138A and 143C, mature upper surface; a blend of 51A and 58B, margins and top 145C, edges of margins 143A and 143B, leaf is heavily and finely dotted with NN137A and 147A, mature lower surface; 51C, margins and top; a blend of 138B and 143C, leaf is heavily blotched with 145C, 145D and 148B.

*Leaf size*.—An average of 7.2 cm in length, 6.8 cm in width.

*Leaf quantity*.—An average of 6 per basal rosette.

*Petioles*.—An average of 13.3 cm in length and 2 mm in diameter, medium strength, both surfaces slightly glossy, upper surface color 144B, as it ages becomes tinged with 152C, lower surface color 146D, surfaces are moderately to densely covered with very short glandular hairs, 0.3 mm in length, NN155D in color.

*Stipules*.—Leafy stipules at the base of each leaf, 1.3 cm in length, 1 mm in width, average length of tip 3 mm, acute, pointing outward in an average angle 90° to peduncle, color of both surfaces 145B and 145C, tinged with 51C and 51D.

Flower description:

*Inflorescence type*.—Axillary compound raceme, numerous small bell-shaped flowers arranged on panicles on peduncles emerging from a basal rosette.

*Inflorescence size*.—An average of 14.8 cm in height and 4.6 cm in diameter.

*Inflorescence number*.—An average of 30.

*Flower fragrance*.—None.

*Flower quantity*.—Average of 49 flowers per inflorescence, 730 flowers and flower buds per plant.

*Flower Lastingness*.—Average of one week.

*Flower buds*.—Obovate to nearly orbicular in shape, an average of 5 mm in length and 2.5 mm in diameter, color; 53C, top 53B, surface is matte and moderately covered with very short glandular hairs an average of 0.2 mm in length and too small to measure color.

*Flower aspect*.—Slightly outward.

*Flower type*.—Single, campanulate.

*Flower size*.—Average of 1 cm in length and 8 mm in diameter.

*Petals*.—Average of 5, rotate arrangement and implanted in the hypanthium at base, oblanceolate in shape, margin is entire, apex is acute, base is acuminate, upper and lower surface are glabrous, smooth and matte, an average of 3 mm in length and 1 mm in width, color; when opening and fully open upper (inner) surface; N57C, when opening and fully open lower surface (outer) N57A.

*Calyx*.—Campanulate, sepals fused to hypanthium, 1 cm in length, 8 mm in diameter.

*Sepals*.—An average of 5, lower 50% fused into campanulate hypanthium, oblong in shape, an average of 9 mm in length and 3 mm in width, margin is entire and fused into hypanthium, apex is obtuse, color; when opening upper surface lower half 55D, upper half 53C, when opening lower surface lower half 53D, upper half 53C, when fully upper surface lower half 56A, upper half 55A, when fully open lower surface lower half 55A, upper half 58C, both surfaces are matte and moderately covered with very short glandular hairs an average of 0.2 mm in length and to small to measure color.

*Peduncle*.—An average of 48.7 cm in length and 2 mm in diameter, color; a blend of 148A and 152A, top 176A, primary flower aspect 75° to horizontal, secondary peduncle aspect to main peduncle 50°, moderate in strength, surface moderately glossy and moderately covered with very short soft glandular hairs; average of 0.2 mm in length and to small to measure color.

*Pedicels*.—An average of 3 mm in length and 0.5 mm in diameter, color; a blend of 183A and N186A, primary flower aspect straight on top of secondary pedicel, secondary and tertiary flower aspect is 45°, moderate in strength, surface matte and moderately covered with very short soft glandular hairs; average of 0.2 mm in length and too small and sparse to measure color.

Reproductive organs:

*Gynoecium*.—Pistils; 2, 3 mm in length, stigma; club-shaped, 0.2 mm in diameter, style; an average of 2.75 mm in length, color is NN155A, base is 158D, ovary; 47B in color.

*Androecium*.—Stamens; 5, anthers; ovate in shape, average of 1 mm in length, 0.75 mm in width, 24B in color, filament; 2.5 mm in length and N155B in color, pollen; moderate in quantity, 24B in color.

*Seed/fruit*.—No fruit or seeds have been observed, flowers are sterile.

It is claimed:

1. A new and distinct cultivar of *Heuchera* plant named 'Snowy Panky' as herein illustrated and described.

* * * * *